(12) United States Patent
Rodger et al.

(10) Patent No.: US 6,422,079 B1
(45) Date of Patent: Jul. 23, 2002

(54) GROUND ANCHORAGE TESTING APPARATUS

(75) Inventors: Albert Alexander Rodger, Aberdeen; Gavin Stuart Littlejohn, Harrogate; Richard David Neilson, Aberdeen; James Penman, Angus, all of (GB)

(73) Assignees: Aberdeen University, Aberdeen; University of Bradford, West Yorkshire, both of (GB)

( * ) Notice: Subject to any disclaimer, the term of this patent is extended or adjusted under 35 U.S.C. 154(b) by 0 days.

(21) Appl. No.: 09/403,913

(22) PCT Filed: Apr. 28, 1998

(86) PCT No.: PCT/GB98/01231
§ 371 (c)(1),
(2), (4) Date: Jan. 27, 2000

(87) PCT Pub. No.: WO98/49553
PCT Pub. Date: Nov. 5, 1998

(30) Foreign Application Priority Data

Apr. 29, 1997 (GB) .............................................. 9708740

(51) Int. Cl.[7] .................................................. G01H 9/00
(52) U.S. Cl. ........................................................ 73/579
(58) Field of Search ....................... 73/579, 594; 367/13

(56) References Cited

U.S. PATENT DOCUMENTS 5,798,981 A * 8/1998 Littlejohn et al. ............. 367/13

FOREIGN PATENT DOCUMENTS

| WO | WO 91/05991 | 5/1991 |
| WO | WO 95/27831 | 10/1995 |

OTHER PUBLICATIONS

Whittington, H. W., "Sonic Testing of Civil Engineering Sub–and Super–Structures," *IEEE Ultrasonics Symposium Proceedings,*1984, 2, 869–876.

* cited by examiner

*Primary Examiner*—Richard A. Moller
(74) *Attorney, Agent, or Firm*—Woodcock Washburn LLP

(57) ABSTRACT

A ground anchorage testing arrangement having an impulse imparting apparatus connectable to a ground anchorage tendon (20) or element thereof to be tested, the impulse imparting apparatus comprising an attachment means (22) for attachment to the ground anchorage tendon (20), a movable mass (31), a guide (28, 34) for guiding movement of the mass in the direction substantially aligned with the axis 0 of the ground anchorage to be tested and a drive means for imparting a driving force to move the mass in said direction (not shown). A method of assessing the integrity of ground anchorages, the method comprising the steps of (a) imparting a load impulse to a ground anchorage tendon to be tested, (b) monitoring the vibrational response signal of the anchorage to the imparted load impulse, (c) conditioning the vibrational response signal and (d) applying the conditioned vibrational response signal to an artificial neural network.

6 Claims, 2 Drawing Sheets

GROUND ANCHORAGE TESTING APPARATUS

FIELD OF THE INVENTION

The present invention relates to a ground anchorage testing system. In particular, the present invention relates to a system for applying a load impulse to ground anchorages and to a system for processing the vibrational response of the anchorages after applying such a load impulse.

BACKGROUND OF THE INVENTION

Known ground anchorages are used to support engineering structures such as tunnels, mines, retaining walls, dry docks and dams. There are two major types of anchorage tendon, solid metal rod type or metal multi wire strand type. To fix an anchorage tendon in the ground, a bore hole is initially made into the sub-surface of the ground. Then, the anchorage tendon is inserted into the bore hole and a length of the part remote from the ground surface is bonded to the ground by resin, cement grout or the like. A further length of the anchorage tendon can also be subsequently bonded to the ground. A tensioning assembly is then positioned against the ground and located on the anchorage tendon so that the anchorage can be post tensioned to an appropriate tension. It will be appreciated that the tensioning assembly varies according to whether the anchorage tendon is of the rod type of multi strand type.

Over time, the post tension on the anchorage may vary for a number of reasons, for example due to gradual movement of the ground, due to sudden movement of the ground consequent to earthquakes, due to deterioration of the anchorage, due to loss of bonding etc. This variation in post tension, generally a loss of post tension, can lead to a local reduction in the support of the structure in question which can eventually build up to a failure to adequately support the structure if sufficient anchorages are affected. Thus, there is a need to assess the continuing integrity of ground anchorages.

WO-A-95/27831, in addition to describing a variety of fixing methods for ground anchorages, also describes a method of assessing the integrity of ground anchorages. An impulse plate is secured to the surf a end of a rod type anchorage and an impulse imparting apparatus is operatively associated with the impulse plate for applying a load impulse to the anchorage. The apparatus involves manually forcing a mass against the tension of a spring, locking the mass in position, and then manually releasing the mass so that the energy of the spring moves the mass to impact the impulse plate thereby causing the anchorage tendon to vibrate. The resultant vibrational response is compared with a reference response from the site of the anchorage at an earlier stage of its life to determine changes in the condition of the anchorage.

However, it will be appreciated that the testing of ground anchorages does not take place at a convenient or easily accessible location. Accordingly, the manual operation of the impulse imparting apparatus is difficult, cumbersome and time consuming. Moreover, the known impulse imparting apparatus is not applicable to multi strand type anchorage tendons. In fact, there is a need to use longer ground anchorages, particularly with respect to withstanding seismic loading, but it has been found that to test ground anchorages in excess of for example 10 metres, the known apparatus can not sufficiently vibrate the anchorage tendon to give a useful vibrational response. Thus, there is a need to apply larger load impulses. Nevertheless, whilst the load impulse applied must be adequate to vibrate the anchorage tendon sufficiently, care must be taken that the load impulse is not then so great as to potentially induce damage to the anchorage.

Accordingly, there is a need for an impulse imparting apparatus which is simple to use, which enables easy variation in the size of the load impulse applied so that the apparatus is versatile in application, and which can be used to apply an impulse load to a multi strand anchorage.

The aforementioned method of assessing the integrity of ground anchorages provides a simple comparison of a vibrational response with a reference vibrational response in order to assess the ground anchorage. In fact, it would be useful to be able to have a more discriminatory assessment of the ground anchorage in terms of the degree of change in post tension. In particular, it would be useful to have an accurate assessment of that change, within say 10% accuracy. The method of assessing the integrity of ground anchorages in WO-A-95/27831 does not provide this.

In addition, as anchorages get longer, it has been found that the accuracy and hence effectiveness of the techniques applied to shorter anchorages is significantly reduced. In particular, for longer ground anchorages, it is increasingly difficult to differentiate between the vibrational responses of the anchorage tendons. Thus, there is a need to improve the differentiation of the vibrational responses for longer ground anchorage tendons.

It is an object of the present invention to provide a ground anchorage testing apparatus having an impulse imparting apparatus which can impart a load impulse appropriate to longer ground anchorages, which can be easily used, and which can easily vary the magnitude of the imparted load impulse.

It is also an object of the present invention to provide a method of assessing the integrity of ground anchorages in which the resolution of the assessment of the vibrational response of the anchorage tendon can be improved sufficiently to provide an improved resolution, particularly in respect of longer ground anchorage tendons.

SUMMARY OF THE INVENTION

According to a first aspect of the present invention there is provided a ground anchorage testing arrangement having an impulse imparting apparatus connectable to a ground anchorage tendon or element thereof to be tested, the impulse imparting apparatus comprising:

an attachment means for attachment to the ground anchorage tendon;

a movable mass;

a guide for guiding movement of the mass in a direction substantially aligned with the axis of the ground anchorage to be tested;

drive means for imparting a driving force to move the mass in said direction.

Preferably, the impulse imparting apparatus comprises a control means for actuating the start of said driving force.

In a preferred embodiment, said driving force is variable.

Conveniently, the driving force is provided by a fluid.

In one embodiment, the fluid comprises compressed air.

It is preferred that the guide comprises an inner cylinder for encircling the anchorage tendon to be tested and a coaxial outer cylinder, and that the movable mass comprises an annular mass with an outer diameter substantially the same as the inner diameter of the outer cylinder and with a central aperture diameter substantially the same as the outer diameter of the inner cylinder.

According to a second aspect of the present invention there is provided a method of assessing the integrity of ground anchorages, the method comprising the steps of:

(a) imparting a load impulse to a ground anchorage tendon to be tested;

(b) monitoring the vibrational response signal of the anchorage to the imparted load impulse;

(c) conditioning the vibrational response signal;

(d) applying the conditioned vibrational response signal to an artificial neural network.

Preferably, step (c) comprises statistical analysis using one or more of the techniques of principal component analysis, wavelet transforms, and higher order spectral analysis.

It is preferred that the method further comprises the step (e) of storing the output from the artificial neural network characteristic of the Conditioned response signal.

Conveniently, the steps (a) to (e) are repeated for a plurality of different tensions on the ground anchorage to provide calibrated characteristics of the output stored in step (e).

In another preferred embodiment, the artificial neural network compares an input conditioned vibrational response signal with calibrated characteristics.

BRIEF DESCRIPTION OF THE DRAWINGS

Examples of the present invention will now be described with reference to the accompanying drawings, in which.

DETAILED DESCRIPTION OF THE PREFERRED EMBODIMENTS

To provide the necessary support, a ground anchorage is installed and the tension T thereon is increased to a predetermined tension $T_{max}$ appropriate for supporting the structure in question. Thereafter, the value of T(t) is a function of time and will vary from $T_{max}$. The ground anchorage integrity testing system of the present invention intends to facilitate the assessment of the value-of T(t) by considering the deviation from $T_{max}$.

Figure 1:
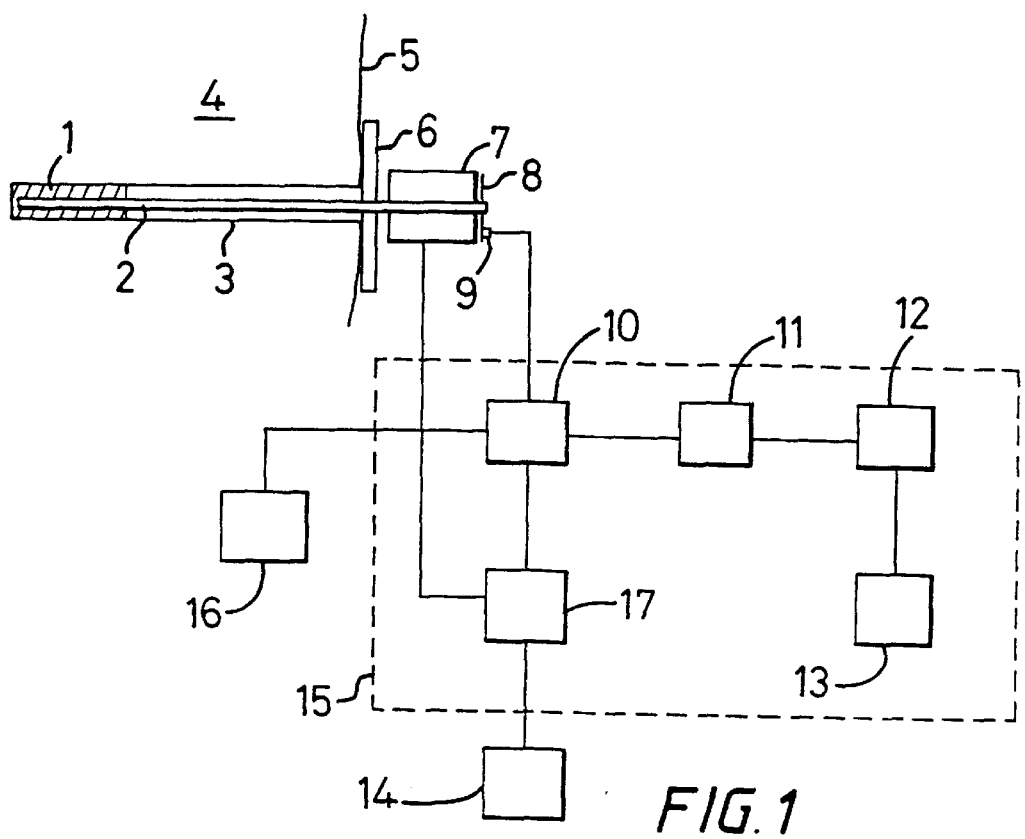
FIG. 1 illustrates a schematic representation of a ground anchorage integrity testing system embodying the present invention.

Referring to FIG. 1, a bore hole 3 is drilled into rock 4 through the rock surface 5. A ground anchorage tendon 2 having a length of 30 metres is inserted into the bore hole. Then, a cement grout is inserted to bond an end length 1 of the anchorage tendon 2 to the rock 4. The space between the remaining length of the anchorage tendon and the rock can be filled with a grout in known manner. A tensioning assembly 6 is located at the anchorage at the rock surface 5. An impulse imparting apparatus 7 is located over the anchorage tendon to impart a load impulse against an impulse plate 8 attached to the anchorage tendon. The impulse plate 8 can form a part of the impulse imparting apparatus. An accelerometer 9 is attached to the impulse plate for detecting the vibrational response of the anchorage. Alternatively the accelerometer 9 could be attached directly to the ground anchorage itself.

The output of the accelerometer is connected to the input of an analysis unit 15. The signals received at the input are * connected to a data acquisition stage 10 which in turn is connected to a statistical processing stage 11. The output from the statistical processing stage 11 is connected to an artificial neural network 12 which can access a memory 13. The analysis unit 15 is controlled by a microprocessor 17 and is connected to a display 16 and an input device 14 such as a keyboard.

The system shown in FIG. 1 operates as follows. The bore hole 3 is made and the anchorage tendon 2 is installed and bonded to the rock. Then, the tensioning assembly and impulse imparting apparatus 7 are mounted to the anchorage tendon 2 together with the impulse plate 8. Thereafter, the anchorage tendon is tensioned to 10% of $T_{max}$. At this point, the microprocessor 17 actuates the load imparting apparatus 7 to provide a suitable load impulse against the impact plate 8 to give a useful vibrational response. The microprocessor 17 controls the data acquisition stage 10 so that the vibration signals from the accelerometer 9 are captured when a predefined trigger point is achieved once the trigger point has been activated, the incoming signal is sampled and filtered to remove noise and unwanted signal attributes.

The output of the data acquisition stage is displayed on the display 16 in both a time and frequency domain format so as to aid the user in selection of data suitable for identification by the unit.

In addition, the output of the data acquisition stage 10 is processed by the statistical stage 11 using a series of mathematical and statistical procedures. This pre-processing uses several techniques such as principal component analysis, wavelet transforms, and higher order spectral analysis. With this use of pre-processing of the signal, it is possible to extract the maximum amount of detail about pertinent aspects of the vibrational response signature whilst minimising unwanted information and noise. Accordingly, the operation of the subsequent artificial neural network is much more accurate in the classification of the vibrational response signatures.

The output of the statistical stage 11 is then relayed to the artificial neural network. The artificial neural network used in the specific embodiment is known as a multi layer perceptron which utilises a supervised learning algorithm called back propagation. This enables the classification of inputs that are not linearly separable and have complicated relationships which are difficult to define with other means. The classification and information regarding the signature is stored in the memory 13.

The microprocessor 17 controls the impulse imparting apparatus 7 such that a series of 20 load impulses are applied to the tensioned anchorage. The number of load impulses can be varied to be different from 20. The optimum vibrational response signatures are selected and processed by the neural network and classified as 10% $T_{max}$ for that location of the anchorage.

Thereafter, the tension on the anchorage is increased by a further 10% $T_{max}$ and the exercise of 20 load impulses is repeated. When the tension reaches 80% $T_{max}$, the increase in tension is reduced to 2% $T_{max}$ before repeating the exercise. Eventually, the tension reaches $T_{max}$ and the anchorage is correctly supporting the structure. The increase in tension can be varied to be different from 2%.

Thus, the artificial neural network has a series of signatures classified according to the anchorage in question and according to tension. The exercise is repeated for a large number of identical anchorages at that location so that the artificial neural network learns to classify the vibrational response signatures with more and more accuracy.

By taking samples in this way with the classification obtained by the system of the present invention, it possible to obtain an improved classification and obtain a higher accuracy of subsequent changes in the integrity of the ground anchorages.

At a later time, for example 6 months later, the system can again be used on the now pre-tensioned anchorages. The exercise of applying a series of 20 load impulses to the anchorages is repeated and by comparison with the classified vibrational response signatures for that anchorage and location in the memory 13 associated with the artificial neural network, it is possible to identify whether there has been a change in the tension on the anchorage tested from the optimum value $T_{max}$ The use of the aforementioned pre-processing step enables identification of the condition of ground anchorages under test with much greater success than hitherto known, and in particular with respect of ground anchorages in excess of say 10 metres.

As described above, to classify and to assess the pre-tension on an anchorage, it is necessary to apply a load impulse I to the ground anchorage tendon. However, it is important that the load impulse I is not more than 20% of $T_{max}$ since otherwise damage to the anchorage may occur. It has been found that I is preferably 5 to 20% of $T_{max}$. However, the value of I will change according to the value of $T_{max}$ for the anchorage in question. Thus, it is important that the load impulse imparting apparatus can easily change the value of the applied load impulse I. Moreover, as mentioned above, in order to obtain a more accurate classification of the vibrational response signature, 20 load impulses are applied to the anchorage to obtain a corresponding number of signatures. Furthermore, for long anchorages in excess of 10 metres, the load impulse applied to the anchorage must be large to obtain a valid vibrational response. Finally, the load impulse imparting apparatus should be able to apply the load impulse to individual strands of a multi strand anchorage tendon.

It has been found that the damping of the vibrational response signature increases with increases in pre-tensioning. By comparing the first 6 peaks of the positive damping envelope over a range of pre-tension levels, it can clearly be seen that the rate of decay of the response signature increases with pre-tension. This makes it possible to differentiate between the various pre-tension levels. In addition, a fast Fourier Transform on the response signatures indicated a change in the main frequency component with a change in pre-tension.

Figure 2:
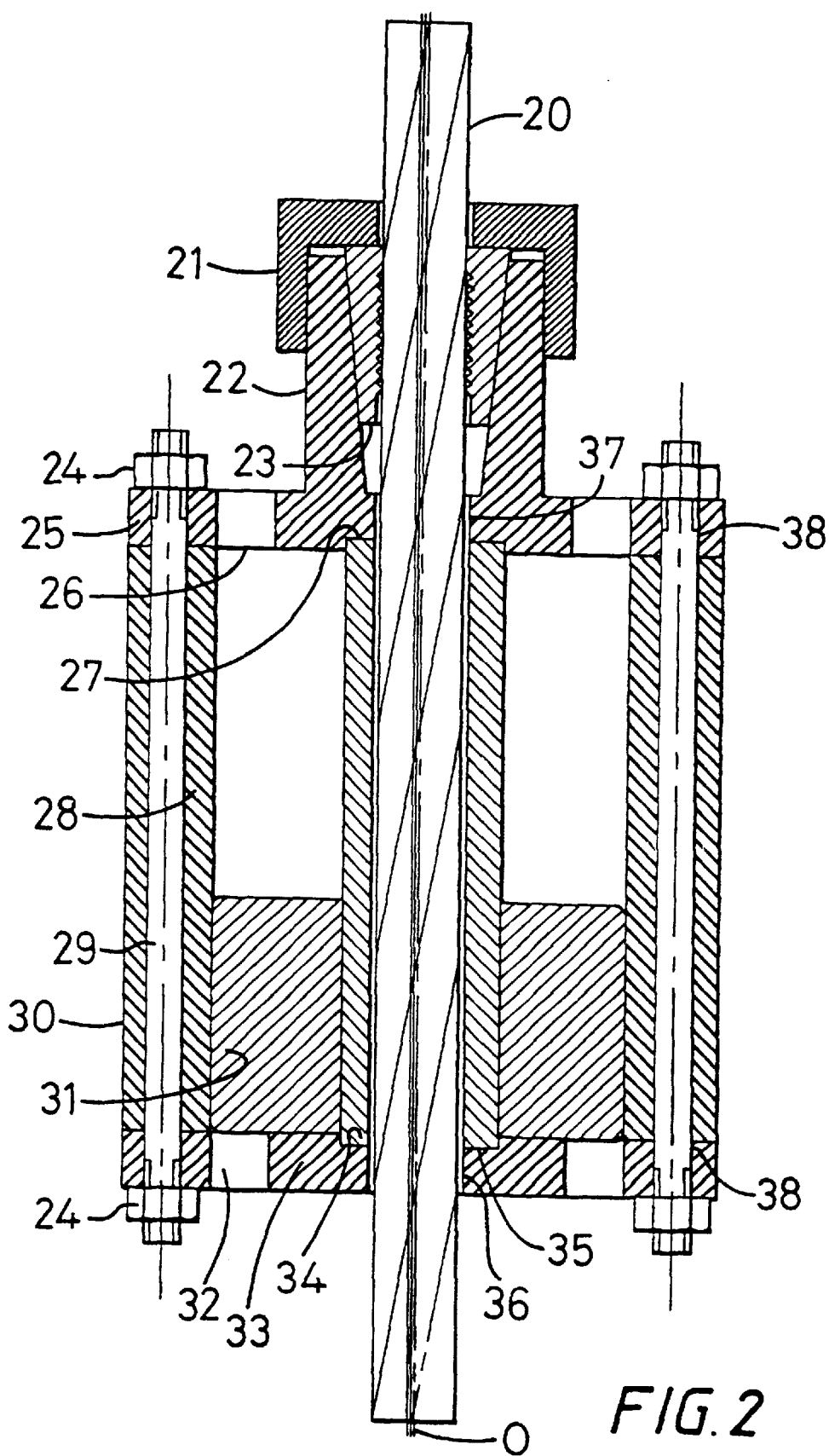
FIG. 2 illustrates an impulse imparting apparatus embodying the present invention.

FIG. 2 illustrates an impulse imparting apparatus embodying the present invention which can impart a load impulse to strands of a multi strand ground anchorage. It will be appreciated that the apparatus can be readily adapted to apply a load impulse to a rod anchorage by having a threaded attachment on the apparatus for screwing the apparatus to the anchorage tendon.

Referring to FIG. 2, the apparatus has an outer cylinder 28 with a first circular end plate 25 at one end and a second circular end plate 33 at the other end. The outer cylinder 28 defines the axis O of the apparatus and locates with an annular recess (not shown) formed in the facing surfaces of the first and second end plates 25 and 33. A hollow inner cylinder 34 extends along this axis and is held in place by further annular recesses 27 and 35 formed in the facing surfaces of the first and second end plates respectively. The inner diameter of the inner cylinder 34 corresponds to the diameter of a tendon 20 of the anchorage to be tested, in this example, a component or strand of a multi strand anchorage. The outer diameter of the inner cylinder substantially corresponds to the diameter of the central aperture in an annular mass 31 which slides along the inner cylinder. The outer diameter of the annular mass 31 substantially corresponds with the inner diameter of the outer cylinder 28. Thus, the annular mass can slide along and be guided by the inner cylinder and also forms a generally airtight seal against both the inner cylinder and outer cylinder.

The first end plate 25 is formed with an anchorage attachment 22. In the present embodiment, this takes the form of a tube integrally formed with the first plate to extend away from the plane of the plate. The tube has an axially located bore with a diameter increasing away from the plane of the first end plate 25 as illustrated. The bore lines up with an aperture 37 centrally located in the first end plate through which the anchorage tendon 20 passes. A plurality of through apertures 26 are formed in the first end plate around the apparatus axis as exhaust ports.

The second end plate 33 also has an aperture 36 centrally located therein through which the anchorage tendon 20 passes. A plurality of through apertures 32 are formed in the second end plate around the apparatus axis as inlet ports.

Both the first and second end plates extend radially beyond the diameter of the outer cylinder and have a plurality of circumferential through apertures 38 at this point. A series of rods 29, which are threaded at both ends, are located through the apertures in both end plates. Nuts 24 are located on the threaded ends of each rod and are tightened to force or clamp the end plates together thereby holding the outer and inner cylinders in place. An outer sleeve 30 is provided around the rods.

In use, the apparatus is located over a strand of a multi strand anchorage to be tested. Then, a set of tapered wedges 23, which are serrated on their axially inwardly facing surfaces, are inserted into the anchorage tendon attachment 22 and are pushed towards the first end plate by a threaded collar 21 which screws onto a corresponding thread formed on the outwardly facing surface of the anchorage tendon attachment 22. Thus, the apparatus grips the strand of the multi strand anchorage so that the apparatus is operatively associated with the anchorage for applying or coupling a load impulse to the anchorage.

A source of compressed air is connected to the inlet ports via switching valves (not shown) controlled by the microprocessor 17. When a load impulse is to be applied to the anchorage, the microprocessor controls the switching valves to introduce compressed air through the inlet ports. This drives the mass to move rapidly from a location adjacent the second end plate towards the first end plate to impact thereon, the movement of the mass being guided by the inner cylinder. Air already within the outer cylinder is expelled from the exhaust ports.

The impact of the annular mass 31 on the first end plate 25 produces a force or load impulse is operatively coupled to the anchorage tendon away from the bonding point in the ground. The mass will then rebound from the first end plate. In order to avoid a second impulse being created on impact with the second end plate, a compression spring (not shown) can be located between the annular mass 31 and the second end plate 35 to damp the rebounding mass. Removal of the spring also facilitates a simple change in the stroke length.

The maximum size of the impulse force can be estimated by the formula:

$$F_{Impact} = \frac{\sqrt{m2l(PA - \text{Friction})}}{\Delta t}$$

where m is the mass of the sliding mass, l is the length of the stroke, P is the applied air pressure, A is the area of the annular mass perpendicular to the axis, Friction is the dry friction on the mass, and $\Delta t$ is the duration of the impact.

Figure 3:
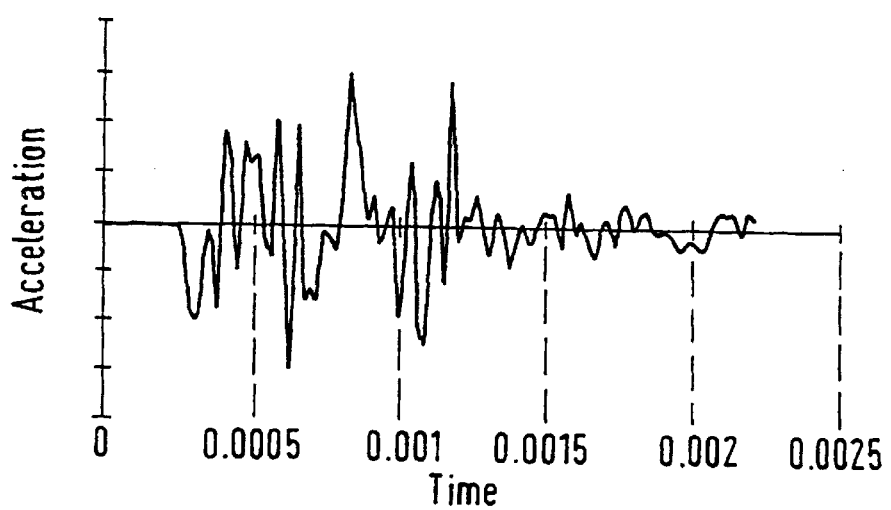
FIG. 3 illustrates a typical accelerometer response signature for an un-tensioned multi strand anchorage.

FIG. 3 illustrates a typical accelerometer response signature for an un-tensioned multi strand anchorage. The values used for the apparatus were as follows:

m=2 Kg
l=140 mm
P=2 Bar
A=$5 \times 10^{-3} m^2$
$\Delta t$=0.1 ms

By driving the mass in this way, it is possible to apply large load impulses to the anchorage sufficient to obtain suitable vibrational response signatures from anchorages in at least the range 10 to 30 metres. Furthermore, the magnitude of the load impulse can be easily varied by controlling the value of P making the apparatus versatile to use. Further variations can be obtained by varying the value of m. It will be understood that the value of m and A will tend to vary since the diameter of the anchorage tendon will change necessitating changes in the inner cylinder, anchorage attachment and mass.

In this respect, it will be appreciated that the apparatus can be easily taken apart to enable different size inner cylinders to be used, different weight masses to be used, different anchorage attachments to be used (for example, a threaded anchorage attachment 22 for attachment to rod anchorages), and to enable variation of the stroke.

In addition, by using a driving force to move the mass, the apparatus can be used from a remote location once the apparatus has been installed. Moreover, it is possible to easily apply a number of load impulses to make the calibration and testing of anchorages very much easier than hitherto. Furthermore, by using the anchorage attachment of the present invention, the apparatus can be used for applying load impulses to strands of multi strand anchorages.

It will be apparent that the present invention can take many forms, the detailed embodiments of which will be readily apparent to a person skilled in the art. For example, hydraulics could be used to drive the mass in the impulse imparting apparatus or an electrical version could be devised.

What is claimed is:

1. A system enabling a user to remotely apply a load impulse to a ground anchorage tendon (2, 20) or element thereof to be tested, the system comprising:

an impact receiver (8, 25) securable relative to the tendon or element thereof so as to operatively transmit mechanical energy therebetween;

a tubular member (34), associated with the impact receiver, encircling the tendon or element thereof and restrained against axial motion relative thereto;

an annular mass (31), disposed coaxially with the tubular member, the mass being capable of sliding movement along the tubular member and being guided thereby towards the impact receiver from an initial position spaced therefrom;

power means (17, 32,33), actuatable remotely from the tendon or element thereof, for applying a particular motive force to the mass to cause the mass to move from said initial position and to collide with the impact receiver thereby generating the load impulse and operatively transmitting it to the tendon or element thereof; and sensor means (9) for detecting the vibrational response of the tendon or element thereof to the load impulse and for generating electrical signals indicative of the response.

2. A system according to claim 1 wherein said power means is operable to vary the magnitude of the motive force by means of which the annular mass is driven along the tubular member.

3. A system according to claim 1 wherein said power means is operable to vary the distance for which the annular mass is driven along the tubular member.

4. A system according to claim 1 comprising a further relatively larger tubular member coaxially aligned with the first-mentioned tubular member, wherein the annular mass has an outer diameter substantially the same as the inner diameter of the relatively large tubular member.

5. A system according to claim 1 wherein said power means comprises a valve arrangement for connecting to a source of hydraulic or pneumatic power.

6. A system according to claim 1 wherein said power means comprises a switch arrangement for connecting to a source of electrical power.

* * * * *

UNITED STATES PATENT AND TRADEMARK OFFICE
CERTIFICATE OF CORRECTION

PATENT NO.   : 6,422,079 B1
DATED        : July 23, 2002
INVENTOR(S)  : Rodger et al.

It is certified that error appears in the above-identified patent and that said Letters Patent is hereby corrected as shown below:

Column 1,
Line 43, please delete "surf a end" and insert -- surface end --;

Column 3,
Line 67, please delete "*";

Column 4,
Line 17, please delete "achieved once" and insert therefor -- achieved. Once --.

Signed and Sealed this

Eleventh Day of February, 2003

JAMES E. ROGAN
*Director of the United States Patent and Trademark Office*